US005763708A

United States Patent [19]
Clemmer et al.

[11] Patent Number: 5,763,708
[45] Date of Patent: Jun. 9, 1998

[54] PROCESS FOR THE PRODUCTION OF DIFLUOROMETHANE

[75] Inventors: Paul Gene Clemmer, Williamsville; Addison Miles Smith, Amherst; Hsueh Sung Tung, Getzville; John Stephen Bass, East Amherst, all of N.Y.

[73] Assignee: Allied Signal Inc., Morris township, Morris County, N.J.

[21] Appl. No.: 530,649

[22] Filed: Sep. 20, 1995

[51] Int. Cl.[6] .................................................. C07C 17/07
[52] U.S. Cl. .................................................. 570/169
[58] Field of Search ........................... 570/165, 166, 570/167, 168, 169

[56] References Cited

U.S. PATENT DOCUMENTS

| | | | |
|---|---|---|---|
| 2,744,148 | 5/1956 | Ruh et al. | 260/653 |
| 2,745,886 | 5/1956 | Ruh et al. | 260/653 |
| 2,748,177 | 5/1956 | Miller et al. | 260/653 |
| 3,862,995 | 1/1975 | Martens et al. | 260/653.6 |
| 4,147,733 | 4/1979 | Fiske et al. | 260/653.4 |
| 5,208,395 | 5/1993 | Elsheikh | 570/166 |

FOREIGN PATENT DOCUMENTS

| | | |
|---|---|---|
| 0 128 510 | 12/1984 | European Pat. Off. |
| 0 508 660 B1 | 10/1992 | European Pat. Off. |
| 95/12563 | 5/1994 | WIPO |
| 94/21579 | 9/1994 | WIPO |

OTHER PUBLICATIONS

Derwent WPI Acc No: 85–028985/05 Abstract for Showa Denko JP 59225131 Dec. 18, 1984.

Patent Abstracts of Japan vol. 18, No. 668 (C-1289), 16 Dec. 1994 and JP.A. 06 263657 (Showa Denko KK), 20 Sep. 1994.

*Primary Examiner*—José G. Dees
*Assistant Examiner*—Alton Pryor
*Attorney, Agent, or Firm*—Lois A. Gianneschi

[57] ABSTRACT

The present invention provides a vapor phase process for the production of difluoromethane, HFC-32. The process of this invention provides for the preparation of HFC-32 by a process that exhibits both good product yield and selectivity.

9 Claims, No Drawings

PROCESS FOR THE PRODUCTION OF DIFLUOROMETHANE

FIELD OF THE INVENTION

The present invention relates to a vapor phase process for the production of difluoromethane, HFC-32. In particular, this invention provides a process for the preparation of HFC-32 that exhibits good product yield and selectivity.

BACKGROUND OF THE INVENTION

It is well known in the art that HFC-32 may be used as a replacement for environmentally disadvantageous chlorofluorocarbon refrigerants, blowing agents, and aerosol propellants. A variety of methods for the vapor phase production of HFC-32 are known.

For example, U.S. Pat. No. 2,745,886 discloses a vapor phase process for fluorinating a variety of halohydrocarbons including methylene chloride, HCC-30, which process utilizes a hydrated chromium fluoride catalyst activated with oxygen. Similarly, U.S. Pat. No. 2,744,148 discloses a halohydrocarbon fluorination process in which an HF-activated alumina catalyst is used.

U.S. Pat. No. 3,862,995 discloses the vapor phase production of HFC-32 by reacting vinyl chloride and HF in the presence of a vanadium derivative catalyst supported on carbon. U.S. Pat. No. 4,147,733 discloses a vapor phase reaction for the production of HFC-32 by HCC-30 with HF in the presence of a metal fluoride catalyst.

In practice, these processes for HFC-32 production suffer from a variety of problems including low product yield and selectivity as well as operational difficulties such as feed decomposition. The process of this invention provides for the production of HFC-32 by a process that overcomes some of the disadvantages of the known processes.

DESCRIPTION OF THE INVENTION AND PREFERRED EMBODIMENTS

The present invention provides a method for HFC-32 production in good yield and selectivity. In general, the process of this invention comprises contacting HCC-30 and HF in the presence of a fluorination catalyst to produce a product stream of difluoromethane, chlorofluoromethane ("HCFC-31"), hydrogen chloride, dichloromethane, and hydrogen fluoride and separating HFC-32 from the product stream. In a preferred embodiment, the invention comprises the steps of:

(A) preheating a composition comprising hydrogen fluoride ("HF") and HCC-30 and, optionally, HCFC-31, to form a vaporized and superheated composition;

(B) reacting the preheated composition of step (A) in the presence of a fluorination catalyst under conditions suitable to form a product stream comprising HFC-32, HCFC-31 and hydrogen chloride and unreacted HCC-30 and HF;

(C) recovering by distillation from the product stream of step (3) a high boiling fraction comprising HF, HCC-30, and HCFC-31 and a low boiling fraction comprising HFC-32, HCl, HF, and reaction byproducts; and (D) recovering substantially pure HFC-32 product from the low boiling fraction of step (C).

In step (A) a composition comprising HF and HCC-30 is preheated in at least one vaporizer. By "preheating" is meant to vaporize and superheat the composition. The composition is heated to a temperature of from about 125° C. to about 400° C., preferably 150° C. to about 300° C., more preferably from about 175° C. to about 275° C. and most preferably 200° C. to about 250° C. The vaporizer, as well as the other vessels used in this process, may be made of any suitable corrosion resistant material.

Although fresh HF and HCC-30 may be used in step (A), preferably the composition of step (A) contains recycled material from step (C) as described below. When the process is run without continuous recycle, the mole ratio of HF to organic, specifically the mole ratio of HF to HCC-30, is from about 1:1 to about 10:1, preferably from about 1:1 to about 4:1. Optionally, fresh HCFC-31 may be added to the composition of step (A).

Alternatively, a continuous recycle stream of the high boiling fraction obtained in step (C) is recycled to step (A) in which case a large excess of HF to organics is used. In the process of this invention, the higher the HF:organics mole ratio, the higher the yield and selectivity for HFC-32. Correspondingly, a large excess of HF will result in the reduction of HCFC-31 produced as well as the concentration of unreacted HCC-30. Additionally, the use of a large excess of HF will decrease catalyst deactivation rates and result in less decomposition in preheaters and vaporizers, especially when the reaction is conducted at pressures in excess of 3 atmospheres. Generally, a ratio of HF to HCFC-31, as measured after separation of HFC-32 from the product stream, of at least about 25:1 to at least about 300:1, preferably at least about 50:1 to at least about 200:1, and more preferably at least about 75:1 to at least about 150:1 is used.

The preheated composition of step (A) is reacted in step (B) in a vapor phase fluorination reaction to form a product stream mixture. The reaction may proceed in one or more isothermal or adiabatic reactors. When more than one reactor is used, the reactor arrangement is not critical, but a sequential arrangement is preferred. Inter-reactor heating or cooling may be used to obtain the best reactor performance.

The reactor or reactors used in this process are filled with a fluorination catalyst and the organic and HF vapor is allowed to contact the catalyst under conditions suitable to form a reaction mixture. The reactor temperature is maintained at from about 125° to about 425° C., preferably 150° C. to about 300° C., more preferably 175° C. to about 275° C. and most preferably 200° C. to about 250° C. Reactor pressure may be atmospheric, subatmospheric, or superatmospheric. Preferably reactor pressure is maintained at from about 0 psig to about 250 psig. Contact time, the time required for the reactants to pass through the catalyst bed assuming a 100% void catalyst bed, is typically from about 1 to about 120 seconds, preferably from about 2 to 60 seconds, more preferably from about 4 to about 50 seconds, and most preferably from about 5 to about 30 seconds.

Any known vapor phase fluorination catalyst may be used in the process of this invention. Exemplary catalysts include, without limitation, chromium, copper, aluminum, cobalt, magnesium, manganese, zinc, nickel and iron oxides, hydroxides, halides, oxyhalides and inorganic salts thereof, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$ and $NiCl_2/AlF_3$. Additionally, supported metal catalysts such as nickel, cobalt, zinc, iron, and copper supported on chromia, magnesia, or alumina may be used. Chromium oxide/aluminum oxide catalysts are described in U.S. Pat. No. 5,155,082 which is incorporated herein in its entirety. Preferably, chromium oxide, a commercially available catalyst, is used. The chromium oxide may be crystalline or amorphous. Preferably, amorphous chromium oxide is used. The catalyst is used in an amount effective to drive the reaction.

The fluorination catalyst may be, and is preferably, pretreated prior to the introduction of the reaction feed stock. By "pretreat" is meant to chemically or physically alter the catalyst in order to create active sites on the catalyst at which the reaction may occur. The catalyst is pretreated by calcining under a flow of inert gas such as nitrogen at a temperature from about 200° C. to about 450° C. for at least about 1 hour. The catalyst is then exposed to HF alone or in combination with up to about 5 to about 99 weight percent of an inert gas at a temperature from about 200° C. to about 450° C. for at least about 1 hour. Preferably, the catalyst then undergoes a third pretreatment step in which it is contacted with chlorine gas. Preferably, the chlorine is diluted with from about 60 to about 75% HF and/or from about 20 to about 30% of an inert gas. The chlorine may be passed over the catalyst at a total volume chlorine to total volume catalyst of about 1:3,000 v/v, preferably about 10:1,000 v/v, more preferably about 50:500 v/v. Exposure time may be from about 1 to about 200 hours, preferably 5 to 70 hours, more preferably 10 to 30 hours. The chlorine exposure may be conducted at any temperature and pressure convenient to the fluorination reaction.

The flow of chlorine is discontinued after pretreatment is complete and the feed HF and HCC-30 introduced. A small amount of chlorine, from about 0.1 to about 10 mol percent based on organic content, preferably from about 2 to about 8 mol percent, may be added to the reactor, preferably while the fluorination reaction proceeds, for periods of time from about 1 to about 200 hours, preferably from about 5 to about 70 hours, and more preferably from about 10 to about 25 hours, should the catalyst become deactivated to restore activity.

The product stream produced in step (B) contains reaction products which are HFC-32, HCFC-31, and HCl as well as unreacted feed stock such as HF and HCC-30. The product stream of step (B) is fed into a recycle column in step (C). The recycle column may be any standard distillation column known in the art. The high boiling fraction, or bottom stream, from the recycle column is composed of unreacted HF and HCC-30 and intermediate reactant HCFC-31. Preferably, this mixture is recycled to step (A) after recovery. Further in step (C), a low boiling fraction, or top stream, of HFC-32, HCl, HF, and reaction byproducts is recovered.

Alternatively, step (C) may be performed in two parts. In the first part, the product stream of step (B) is quenched. By "quenching" is meant that the temperature of the reaction mixture is reduced to below its dew point. Quenching may be conducted in a packed column containing any suitable corrosion resistant packing material and a suitable refluxing liquid such as HF, HCC-30, and/or HCFC-31 after which the quenched product is fed into the recycle column.

In step (D), substantially pure HFC-32 is recovered from the low boiling fraction of step (C) by any method well known in the art. Preferably step (D) is performed by a series of substeps including step (E), treating the gaseous mixture in an HCl distillation column or aqueous HCl absorption tower under conditions suitable to remove HCl and trace HF. The crude HFC-32 product of step (E) is then treated in step (F) with a first caustic scrubber under conditions suitable to form a neutralized product by neutralizing residual acidity. Typically, the caustic scrubber contains water, sodium hydroxide, or potassium hydroxide. Step (F) is followed by step (G) in which the step (F) product is treated in a second caustic scrubber, preferably comprising sodium hydroxide together with a sulfite, such as sodium sulfite under conditions suitable to remove residual chlorine and form a substantially chlorine-free product. In step (H), the step (G) product is treated with a sulfuric acid scrubber followed by a solid desiccant, such as any suitable, commercially available, molecular sieve that absorbs residual moisture from the gas stream to form a substantially moisture-free product. This is followed by step (I) in which the step (H) product is conducted through a plurality of distillation columns under conditions sufficient to remove the residual impurities and produce substantially pure HFC-32, greater than 99.97 weight percent. Any residual HCFC-31 removed in step (I) may be recycled to step (A).

The following non-limiting examples will serve to clarify and exemplify the process of this invention.

Examples 1 and 2

In a ½ inch Monel pipe reactor, about 110 ml $Cr_2O_3/Al_2O_3$ (40/60 wt %) co-extruded catalyst were packed. The catalyst was dried/calcined at about 400° C. for about 16 hours using air at 2-3 liters per minute. Then, the temperature was lowered to 200° C. and air was replaced with nitrogen at about 0.5-1.5 liters per minute. Anhydrous HF was pumped into the reactor at about 1-2 ml/min until exotherm passed through the reactor. Subsequently, temperature was raised at 25° C. every half hour until the temperature was about 350°-40° C. and held there for 8 hours. Temperature was then lowered to the desired reaction temperature. HF and HCC-30 were fed into the reactor at a molar ratio of 4:1 (HF:HCC-30). The mixture of HF and HCC-30 passed through two preheaters, the first of which was at about 100°-185° C. and the second at about 200°-275° C. The pressure was 50 psig and reactor temperature was 275° C. for Example 1 and 300° C. for Example 2. For Example 1, contact time was 16 seconds resulting in 82% conversion and 89.3% HFC-32 selectivity. The productivity was 10 lbs HFC-32/hr/ft³. Contact time for Example 2 was 10 seconds and HCC-30 conversion decreased to 77%. HFC-32 productivity for Example 2 was 13.6 lbs/hr/ft³ and HFC-32 selectivity was about 85%. The results of these examples are summarized on Table I.

TABLE I

| Catalyst | Example 1 $Cr_2O_3/Al_2O_3$ (40/60 wt %) | Example 2 $Cr_2O_3/Al_2O_3$ (40/60 wt %) |
|---|---|---|
| Pressure | 50 psig | 50 psig |
| HF/HCC-30 | 4 | 4 |
| Temperature °C. | 275 | 300 |
| Contact Time (sec.) | 16 | 10 |
| Conversion % $CH_2Cl_2$ | 82 | 77 |
| Selectivity (%): | | |
| HFC-32 | 89.3 | 84.7 |
| HCFC-31 | 10.6 | 15.2 |
| HCC-40 | 0.1 | 0.1 |
| Productivity (lbs/hr/ft³): | | |
| HFC-32 | 10.3 | 13.6 |

Examples 3-6

In the pipe reactor of Examples 1 and 2, about 100-110 ml $Cr_2O_3/Al_2O_3$ catalyst of 78/22 weight percent ratio was packed. The catalyst was dried/calcined and HF-treated using the same procedure as for Examples 1 & 2. HF and HCC-30 were fed into the reactor at a 4:1 (HF/HCC-30) ratio. A mixture of HF and HCC-30 was passed through the same preheaters indicated in Examples 1 & 2. Pressures, contact times, and the results are shown on Table II.

TABLE II

| Catalyst | Example 3 $Cr_2O_3/Al_2O_3$ (78/22 wt %) | Example 4 $Cr_2O_3/Al_2O_3$ (78/22 wt %) | Example 5 $Cr_2O_3/Al_2O_3$ (78/22 wt %) | Example 6 $Cr_2O_3/Al_2O_3$ (78/22 wt %) |
|---|---|---|---|---|
| Pressure (psig) | 50 | 200 | 225 | 225 |
| HF/$CH_2Cl_2$ mole ratio | 4 | 4 | 4 | 4 |
| Temperature (°C.) | 275 | 275 | 275 | 275 |
| Contact Time (sec) | 11 | 36 | 40 | 26 |
| Conversion (% $CH_2Cl_2$) | 71 | 70 | 70 | 61 |
| Selectivity: | | | | |
| HFC-32 | 82 | 81 | 81 | 77 |
| HCFC-31 | 18 | 19 | 19 | 23 |
| HCC-40 | 0.05 | 0.05 | 0.05 | 0.05 |
| Productivity (lbs/hr/ft³): | | | | |
| HFC-32 | 12 | 12 | 12 | 15 |

Example 7

A 4 inch diameter Monel 400 reactor was charged with 4 liters of 5 chromium oxide catalyst. The catalyst was dried under 20 slpm nitrogen flow at a temperature of 350° C. for 8 hours. After reducing the catalyst bed temperature to 250° C., anhydrous HF was added to the flowing nitrogen at a flow rate of 0.2 lbs/hr. The HF flow rate was gradually increased to 1.0 lb/hr and the temperature increased to 350° C. and held for 4 hours. The catalyst bed temperature was then decreased to 250° C. and chlorine introduced to the HF/$N_2$ mixture at a rate of 500 sccm for a period of 24 hours.

After this pretreatment procedure, the chlorine and nitrogen flows were discontinued and HCC-30 was mixed with HF and passed though a preheater at 185° C. The vaporized HCC-30 and HF mixture was fed to the reactor at a pressure of 45 psig. the effluent from the reactor was quenched using a heat exchanger and fed into a distillation column maintained at 50 psig. The low boiling distillation components, HCFC-31, HF, and HCC-30 were recycled back to mix with fresh HF and HCC-30 feed stream and were fed to the preheater, and the reactor at a flow rate of 4.6 lbs/hr. The recycle stream contained a molar ratio of HF:HCFC-31 of 360:1. The recycle material was mixed with additional HF and HCC-30 at flow rates of 0.5 and 1.0 lbs/hr, respectively, before being passed over the catalyst. The resulting contact time was 12 seconds. The low boiling components separated in the distillation column, HCl and HFC-32, were passed through a caustic scrubber containing 10% KOH where HCl was removed. The purified HFC-32 was dried and collected. The resulting HCC-30 conversion was 90% with 90% selectivity to HFC-32 and 9% selectivity to HCFC-31.

What is claimed is:

1. A process for producing difluoromethane comprising the steps of:

(A) preheating a composition comprising hydrogen fluoride and dichloromethane to form a vaporized and superheated composition;

(B) reacting the preheated composition of step (A) in the presence of a fluorination catalyst under conditions suitable to form a product stream comprising difluoromethane, chlorofluoromethane, hydrogen chloride, dichloromethane and hydrogen fluoride;

(C) recovering by distillation from the product stream of step (B) a high boiling fraction comprising hydrogen fluoride, dichloromethane, and chlorofluoromethane and a low boiling fraction comprising difluoromethane, hydrogen chloride, hydrogen fluoride, and reaction byproducts; and (D) recovering substantially pure difluoromethane from the low boiling fraction of step (C) comprising the substeps of:

(i) treating the low boiling mixture of step (C) in an HCl distillation column or an aqueous HCl absorption tower under conditions suitable to remove HCl and trace HF to form a crude HFC-32 product;

(ii) treating the crude HFC-32 product formed in step (i) with a first caustic scrubber under conditions suitable to form a neutralized product;

(iii) treating the neutralized product of step (ii) in a second caustic scrubber under conditions suitable to form a substantially chlorine-free product;

(iv) treating the substantially chlorine-free product of step (iii) with a sulfuric acid scrubber and subsequently with a solid desiccant to form a substantially moisture-free product; and (v) distilling the substantially moisture-free product of step (iv) under conditions suitable to produce substantially pure difluoromethane.

2. The process of claim 1 wherein the high boiling fraction of step (C) is recycled to step (A).

3. The process of claim 1 wherein the hydrogen fluoride and dichloromethane are present in a mole ratio of from about 1:1 to about 10:1.

4. The process of claim 1 wherein the composition of step (A) further comprises chlorofluoromethane.

5. The process of claims 4, 2, or 1 wherein the hydrogen fluoride and the chlorofluoromethane are present in the product stream in a mole ratio of at least about 25:1 to at least about 300:1.

6. The process of claims 4, 2, or 1 wherein the hydrogen fluoride and the chlorofluoromethane are present in the product stream in a mole ratio of at least about 50:1 to at least about 200:1.

7. The process of claims 4, 2, or 1 wherein the hydrogen fluoride and the chlorofluoromethane are present in the product stream in a mole ratio of at least about 75:1 to at least about 150:1.

8. The process of claim 1 wherein the fluorination catalyst is a pretreated fluorination catalyst.

9. The process of claims 8 or 1 wherein the fluorination catalyst is chromium oxide.

* * * * *

UNITED STATES PATENT AND TRADEMARK OFFICE
CERTIFICATE OF CORRECTION

PATENT NO : 5,763,708
DATED : June 9, 1998
INVENTOR(S): Clemmer et al.

It is certified that error appears in the above-identified patent and that said Letters Patent is hereby corrected as shown below:

Col. 1, Line 57, "Step (3)" should read --step (B)--

Col. 4, Line 25, "350°-40°C." should read --350°-400°C--

Col. 5, Line 26, "liters of 5 chromium" should read -- liters of chromium--

Signed and Sealed this

Twenty-fourth Day of November, 1998

*Attest:*

BRUCE LEHMAN

*Attesting Officer*  *Commissioner of Patents and Trademarks*